(12) United States Patent
Beach (10) Patent No.: US 10,064,563 B2
(45) Date of Patent: Sep. 4, 2018

(54) APPARATUS AND METHODS FOR DETECTING INCREASE IN INTRACRANIAL PRESSURE

(71) Applicant: NIHON KOHDEN CORPORATION, Tokyo (JP)

(72) Inventor: Kirk Watson Beach, Seattle, WA (US)

(73) Assignee: NIHON KOHDEN CORPORATION, Tokyo (JP)

( * ) Notice: Subject to any disclaimer, the term of this patent is extended or adjusted under 35 U.S.C. 154(b) by 308 days.

(21) Appl. No.: 14/737,461

(22) Filed: Jun. 11, 2015

(65) Prior Publication Data

US 2015/0359448 A1    Dec. 17, 2015

Related U.S. Application Data

(60) Provisional application No. 62/010,590, filed on Jun. 11, 2014.

(51) Int. Cl.

| A61B 5/00 | (2006.01) |
|---|---|
| A61B 5/03 | (2006.01) |
| A61B 5/11 | (2006.01) |
| A61B 5/0205 | (2006.01) |
| A61B 8/08 | (2006.01) |
| A61B 5/024 | (2006.01) |
| A61B 5/08 | (2006.01) |

(Continued)

(52) U.S. Cl.
CPC ............. *A61B 5/031* (2013.01); *A61B 5/024* (2013.01); *A61B 5/0205* (2013.01); *A61B 5/08* (2013.01); *A61B 5/11* (2013.01); *A61B 5/4064* (2013.01); *A61B 8/0808* (2013.01); *A61B 8/15* (2013.01); *A61B 5/0082* (2013.01); *A61B 5/053* (2013.01); *A61B 8/5207* (2013.01); *A61B 8/5223* (2013.01)

(58) Field of Classification Search
CPC .................................. A61B 5/03; A61B 5/031
See application file for complete search history.

(56) References Cited

U.S. PATENT DOCUMENTS

| 5,617,873 A | 4/1997 | Yost et al. |
| 6,875,176 B2 * | 4/2005 | Mourad ............... A61B 5/0048 600/442 |
| 7,621,878 B2 | 11/2009 | Ericson et al. |

(Continued)

FOREIGN PATENT DOCUMENTS

| EP | 0 413 816 A1 | 2/1991 |
| WO | 99/12473 A1 | 3/1999 |
| WO | 2010/014815 A1 | 2/2010 |

OTHER PUBLICATIONS

Extended European search report for the related European Patent Application No. 15805805.7 dated Jan. 25, 2018.

*Primary Examiner* — Max Hindenburg
(74) *Attorney, Agent, or Firm* — Kenealy Vaidya LLP (57) ABSTRACT

The disclosed subject matter related to methods and apparatus for determining brain swelling in a patient as well as predicting an increase in intracranial pressure in the patient. The apparatus can include a transducer such as an ultrasound transducer communicatively connected to a controller via wires or via wireless communications device(s). A monitor and/or alarm device can be provided to notify a practitioner when the controller has determined brain swelling is occurring and/or when an imminent increase in intracranial pressure is likely to occur.

8 Claims, 11 Drawing Sheets

(51) Int. Cl.
*A61B 8/15* (2006.01)
*A61B 5/053* (2006.01)

(56) References Cited

U.S. PATENT DOCUMENTS

| | | | |
|---|---|---|---|
| 9,351,640 B2 * | 5/2016 | Tran | G06F 19/3418 |
| 2002/0060633 A1 | 5/2002 | Crisco, III et al. | |
| 2009/0069700 A1 | 3/2009 | Eide | |
| 2009/0149751 A1 | 6/2009 | Mourad et al. | |
| 2010/0145201 A1 | 6/2010 | Westbrook et al. | |
| 2010/0204589 A1 | 8/2010 | Swoboda et al. | |
| 2010/0331684 A1 | 12/2010 | Ragauskas et al. | |
| 2013/0018277 A1 | 1/2013 | Liu | |

* cited by examiner

Fig. 6b
Respiratory Cycle

Figure 6a
Brain Motion Cardiac Cycle

APPARATUS AND METHODS FOR DETECTING INCREASE IN INTRACRANIAL PRESSURE

The present application is a non-provisional application and claims priority under 35 U.S.C. 119 to provisional application No. 62/010,590 filed on Jun. 11, 2014, the entirety of which is hereby incorporated by reference.

BACKGROUND

The disclosed subject matter relates to methods, kits, and devices for detecting swelling of the brain in a patient. More particularly, the disclosed subject matter relates to methods, kits and devices configured for ensuring easy and repeatable procedures for identifying intracranial tissue swelling in order to predict when an increase in intracranial pressure (ICP) will occur. Increased ICP can arise as a consequence of various traumas, diseases or congenital defects, and can be a result of intracranial mass lesions, disorders of cerebrospinal fluid (CSF) circulation, as well as more diffuse intracranial pathological processes. For example, in some cases, increased ICP is caused by obstruction of the outflow of Cerebral Spinal Fluid (CSF). This obstruction causes the ventricles to expand resulting in hydrocephalus.

The brain typically includes four fluid-filled ventricles which are connected. These cavities, known collectively as the ventricular system, include or consist of the left and right lateral ventricles, the third ventricle, and the fourth ventricle. The fourth ventricle extends from the cerebral aqueduct (aqueduct of Sylvius) to the obex, and is filled with CSF. The fourth ventricle has a characteristic diamond shape in cross-sections of the human brain. The fourth ventricle is located within the pons or in the upper part of the medulla. CSF entering the fourth ventricle through the cerebral aqueduct can exit to the subarachnoid space of the spinal cord through two lateral foramina of Luschka and a single, midline foramen of Magendie.

The fourth ventricle is an outpouching on the posterior part of the brainstem. The flow of CSF to the nasal submucosal lymphatic channels occurs through the cribriform. When CSF pressure is elevated, cerebral blood flow may be constricted. CSF entering the fourth ventricle through the cerebral aqueduct can exit to the roof of the fourth ventricle formed by the cerebellum (and can expand into lateral, third and fourth ventricles, connected by thinner channels). Expansion of the ventricles is called Hydrocephalus and can lead to an increase in intracranial pressure. Congenital hydrocephalus is present in about 0.1% of newborn children and is due to outflow obstruction. Acquired Normal Pressure Hydrocephalus (NPH), due to excessive production of CSF, is present in an estimated 0.5% of adults over the age of 65, is underdiagnosed, and can cause gait disturbances, urinary incontinence and dementia.

Alternatively, expansion of intracranial solid tissues including: [1] brain cell swelling (cerebral edema) from infectious, hemodynamic, pharmacologic, metabolic or traumatic causes, [2] brain tumors, and [3] subdural or epidural hematomas from minor head trauma, can cause collapse of the ventricles; continued expansion results in increased ICP.

In both hydrocephalus (ventricular inflation) and intracranial tissue expansion, the first compensation is the obliteration of the layer of CSF surrounding the brain. The obliteration of this layer typically precedes an increase in ICP.

While normal ranges for ICP vary with age, increases in ICP can be acute or chronic, and thresholds for treatment are often difficult to determine.

The relation between volume and pressure within the cranium is non-linear. The Monro-Kellie hypothesis states that the sum of the intracranial volumes of blood, brain, CSF, and other components (for example, tumor, hematoma) is constant. The skull can be considered to be an inelastic container. An increase in the volume of any one of the intracranial contents is typically offset by a decrease in one or more of the others, ultimately leading to an increase in ICP. Intracranial blood (especially in the venous/venular compartment) and CSF are two low pressure components whose volume can adapt easily to accommodate an increase in the volume of intracranial contents. Once the change in volumes of intracranial blood and CSF are exhausted, further increases in volume result in increase in ICP. Changes in both arterial and venous compartments affect pressure. Sitting up to an inclined position to raise the brain 20 cm above the heart results in ICP reduction by 8 mmHg due to deflation of the veins and venules; the expansion of intracranial arteries and arterioles by about 5 milliliters after each heart beat raises ICP by 1 mmHg. Compliance (the change in volume for a given change in pressure) provides an index of compensatory reserve, with low values suggesting a diminished reserve. Compliance is reduced when ICP is elevated, at an abnormal ICP of 25 mmHg, the arterial pressure ICP pulsation is 4 mmHg.

Conventionally, emergency room personnel and intensive care practitioners could deliver better care if ICP could be measured or monitored in a patient presenting with certain conditions such as head trauma or neurological symptoms. Unfortunately, monitoring ICP is typically accomplished through the use of a manometer that is inserted into a hole drilled into the skull of the patient. Thus, monitoring ICP requires an invasive procedure undertaken by a neurosurgeon (or at least with a neurosurgeon available in case of complications or difficulties with the surgery), because the procedure exposes the patient to infection and other inherent surgical risks. In addition to the difficulty in obtaining and monitoring ICP, there are also certain drawbacks to relying solely on ICP for diagnosis and treatment of trauma. For example, relying solely on ICP data may cause a time delay in treatment, may require complicated diagnostic and monitoring protocols, and may be subject to false readings should the instrumentation for monitoring ICP not be set up correctly or otherwise fail or be interpreted improperly.

SUMMARY

Although ICP is an important variable for patient management, it is equally valuable to understand and possibly monitor and/or determine any causative variables associated with increases in ICP. Increases in ICP can be caused, in certain instances, by swelling of the brain tissues (edema) or by the expansion of tissue in the brain, for example, due to infection, injury, tumor, blood clot, or obstruction of cerebrospinal fluid (CSF) flow (hydrocephalus). Monitoring of brain swelling, other intracranial tissue swelling and/or ventricular expansion can provide information helpful in predicting an imminent increase in ICP, as well as extent of ICP increase, and can therefore provide a practitioner timely information to initiate therapy and to monitor the effectiveness of that therapy.

Swelling or enlarging of the brain will occur substantially freely within an approximately 1 mm thick cushion of cerebral fluid that surrounds the brain. However, after a point at which the brain either fills the calvarium, or meets resistance at an anchor or tether point, the brain runs out of room to further expand or swell, and ICP will then begin to increase. It is at this point, when the brain meets resistance from the skull or tether points in the skull, that motion of the brain with respect to the boundaries due to swelling will decrease. This decrease in relative motion of the brain can then be used as an indicator that ICP will soon increase.

One hypothesis states that the sum of the intracranial volumes of blood, brain, CSF, and other components (for example, tumor, hematoma) is constant. The skull is considered as an enclosed and inelastic container. An increase in the volume of any one of the intracranial contents is typically offset by a decrease in one or more of the others, or is associated with a rise in ICP. Intracranial blood (especially in the venous compartment) and CSF are the two components whose volume can adapt most easily to accommodate an increase in the volume of intracranial contents.

According to an aspect of the disclosed subject matter, certain methods and kits and apparatus are provided that allow a standardized procedure in which normal brain motions and pulsations restricted by brain swelling can be determined and/or monitored in various conditions, regardless of operator ability or input.

According to another aspect of the disclosed subject matter, a kit for predicting intracranial pressure increase in a patient can include placing a transducer adjacent a brain, determining at least one of location and velocity of a first tissue portion relative to at least one of location and velocity of a second tissue portion based on information received by the ultrasound transducer, and predicting an increase in intracranial pressure based on at least one of the location and the velocity of the first tissue portion relative to the at least one of the location and the velocity the second tissue portion.

According to another aspect, a method of predicting intracranial pressure increase in a patient, can include placing an ultrasound transducer adjacent a skull, determining at least one of location and velocity of a first tissue portion relative to at least one of location and velocity of a second tissue portion based on information received by the ultrasound transducer, and predicting an increase in intracranial pressure based on information that movement of the first tissue portion relative to the second tissue portion has decreased.

According to another aspect, a method of predicting intracranial pressure increase in a patient, can include placing a transducer (such as an ultrasound, optical or impendence transducer) on the skin enclosing the skull and transmitting the energy beam pattern directed into a brain, determining at least one of location and velocity of a first brain tissue portion relative to the skull, and predicting an increase in intracranial pressure based on information that movement of a brain tissue portion relative to the skull has decreased.

According to another aspect, an apparatus for predicting intracranial pressure increase in a patient can include an ultrasound transducer, at least one of a monitor and an alarm device, and a controller communicatively connected to both the transducer and the at least one of the monitor and the alarm device. The controller can be configured to receive information from the transducer related to at least one of a location and a velocity of a first tissue portion relative to at least one of a location and a velocity of a second tissue portion. The controller can be further configured to predict an increase in intracranial pressure based on information that movement of a first tissue portion relative to a second tissue portion has decreased, and the controller can be configured to output a signal to at least one of the monitor and the alarm device if the controller predicts the increase in intracranial pressure. Although the apparatus and method are effective in predicting intracranial pressure increase due to brain swelling, the method can also be effective in predicting other increases in pressure such as due to compartment syndrome of muscles in the legs or arms, which is similar in most respects (a limited containing volume, enclosing expanding tissue or fluid space which results in the loss of blood supply (ischemia) and tissue death).

BRIEF DESCRIPTION OF THE DRAWINGS

The disclosed subject matter of the present application will now be described in more detail with reference to exemplary embodiments of the apparatus, kits and method, given by way of example, and with reference to the accompanying drawings, in which.

DETAILED DESCRIPTION OF EXEMPLARY EMBODIMENTS

A few inventive aspects of the disclosed embodiments are explained in detail below with reference to the various figures. Exemplary embodiments are described to illustrate the disclosed subject matter, not to limit its scope, which is defined by the claims. Those of ordinary skill in the art will recognize a number of equivalent variations of the various features provided in the description that follows.

1. Exemplary Method and Apparatus for Predicting Increase in Intracranial Pressure The cranial braincase is a fixed volume containing "semi-solid" neurological tissue and other solids plus liquid blood and cerebral-spinal fluid. The only major outlet is the foramen magnum containing the brainstem including channels for CSF flow to and from the ventricles to the spinal cord. Blood vessels provide additional communications between the calvarium and the exterior. The current standard of practice for assessing intracranial pathology includes the measurement of Intra-Cranial Pressure (ICP). Intracranial pressure can be reviewed in various time increments, such as seconds (C waves), minutes (B waves), fractions of hours (A waves), or on a daily basis, to provide information about the likely outcome of the case and to provide information necessary for treatment. ICP is measured in various types of cases, such as stroke, osmotic metabolic disease, unexplained coma, hydrocephalus, and head trauma. Some publications suggest that ICP measurement would be useful in the evaluation of severe headache, gait disturbances, incontinence and dementia.

In the case of head trauma, the time course of ICP can be correlated with patient outcome. For example, in cases considered to have an "early profile" where ICP was elevated for two days or less, the patient outcome was relatively good. In cases considered to have an "intermediate profile" where ICP was elevated for a time period between two and five days, the patient outcome was not as good as in early profile cases. In cases considered to have a "late profile" where ICP was elevated greater than five days, the patient outcome was more often severe, including vegetative state and death. In addition, if a mass were removed from the brain or skull during treatment, the number of intermediate profile cases dropped from 40% to 12%, while the early and late profile cases increased from 25% to 40% and from 35% to 50%, respectively. Thus, patient outcome was related to the ICP profile: good outcome was rare in "late profile" cases compared to "early profile." Death, persistent vegetative state and severe disability were higher in "late profile" cases compared to "early profile" cases.

The cause of the poor outcome correlation with long duration High ICP might be due to brain tissue ischemia due to low Cerebral Perfusion Pressure (CPP), the difference between Blood Pressure (BP) and ICP.

$$CPP=BP-ICP$$

CPP is similar to transmural pressure (BP—tissue pressure) that sustains inflation of arteries and veins. Transmural pressure is related to muscle compartment syndrome, in which elevated tissue pressure due to edema within a confined fascial compartment compresses the patency of veins and arteries. Because the vascular walls are flaccid, the lumen collapses as the tissue pressure exceeds the luminal pressure.

CPP analysis considers the contents of the cranium to be liquid with isotropic, uniform pressure distribution, a simplification that might obscure a better understanding. Thus the ICP measurement from a single point might not be sufficient to characterize the pressure throughout the volume of the cerebrum and cerebellum because the major content of the cranium is semi-solid, tethered at multiple locations, and divided by fascia into compartments.

As a mass or swelling expands in a portion of the brain, the solid tissue will distort and deflect the boundaries creating differing regions of pressure within the cranium. In addition, tethering will create further alterations in pressure. One example of tethering is the Superior Sagital Sinus, which has a negative transmural pressure, but is stretched open by the tether of the Falx Cerebri. Of course, in solid tissue, pressure is not isotropic (equal in all directions). The differences in pressure in different regions of the brain will cause the arterial, arteriolar, venular and venous transmural pressure to differ between regions. Low transmural pressure in one region might decrease or obstruct perfusion in that region while other regions receive higher perfusion, causing the regions of decreased perfusion to become ischemic resulting in regional brain damage. In the supine patient, where venous drainage to the right atrium is via open veins and thus the respiratory variations in atrial pressure are reflected in the cerebral venules, an increase in pressure in a portion of the brain will result in adverse venular transmural pressure and a decrease in the respiratory tissue volume changes. This condition will also result in an increase in arteriolar pulse amplitude, as the "cushioning effect" of the venules is lost. In a patient with more severe regional cerebral pressure increases, the arteriolar transmural pressure might become unfavorable leading to a loss of brain perfusion indicated by the loss of the tissue arteriolar pulsations. Applicant notes that if the ICP exceeds the arterial pressure, especially exceeds the systolic brain arterial pressure (arm blood pressure (=120 mmHg)–Elevation hemostatic decrease (=30 mmHg~40 cm Elevation)=90 mmHg, then the brain strain pulse amplitude should decrease to zero, when the ICP is between diastolic and systolic pressure, then the pulsatile strain should be large.

There is also a possibility of regional perfusion that could be monitored or predicted in accordance with the presently disclosed subject. Because the pressure is likely to be different in different compartments of the cranium, a region of increased pressure might have depressed perfusion compared to another.

In addition, it is possible that "slow waves" exist that can be measured on the order of a minute or so, that are due to major shifts of tissue, releasing "bottled up" pressure, that are likely similar to "earthquakes" that will cause large brain motions. Certain noise filters can be incorporated into the software and/or hardware of the disclosed subject matter in order to protect data from being swamped or somehow made less effective by these "earthquake" type of events.

In pathological cases, ICP increases by various mechanisms, including for example: 1) the obstruction of outflow of Cerebral Spinal Fluid (CSF) leading to hydrocephalus; 2) the expansion of solid tissue including: 2a) brain edema, 2b) intracranial hematoma, and 2c) tumor.

Some in-vivo models of ICP have measured "brain elasticity" (dP/dV) by the infusion of fluid into brains or spinal cords, assuming that the brain tissue is compressible or that the vascular and fluid spaces in the cranium have elastic boundaries. Here we consider an alternate conception of the cranio/cerebral dynamics.

Figure 1:
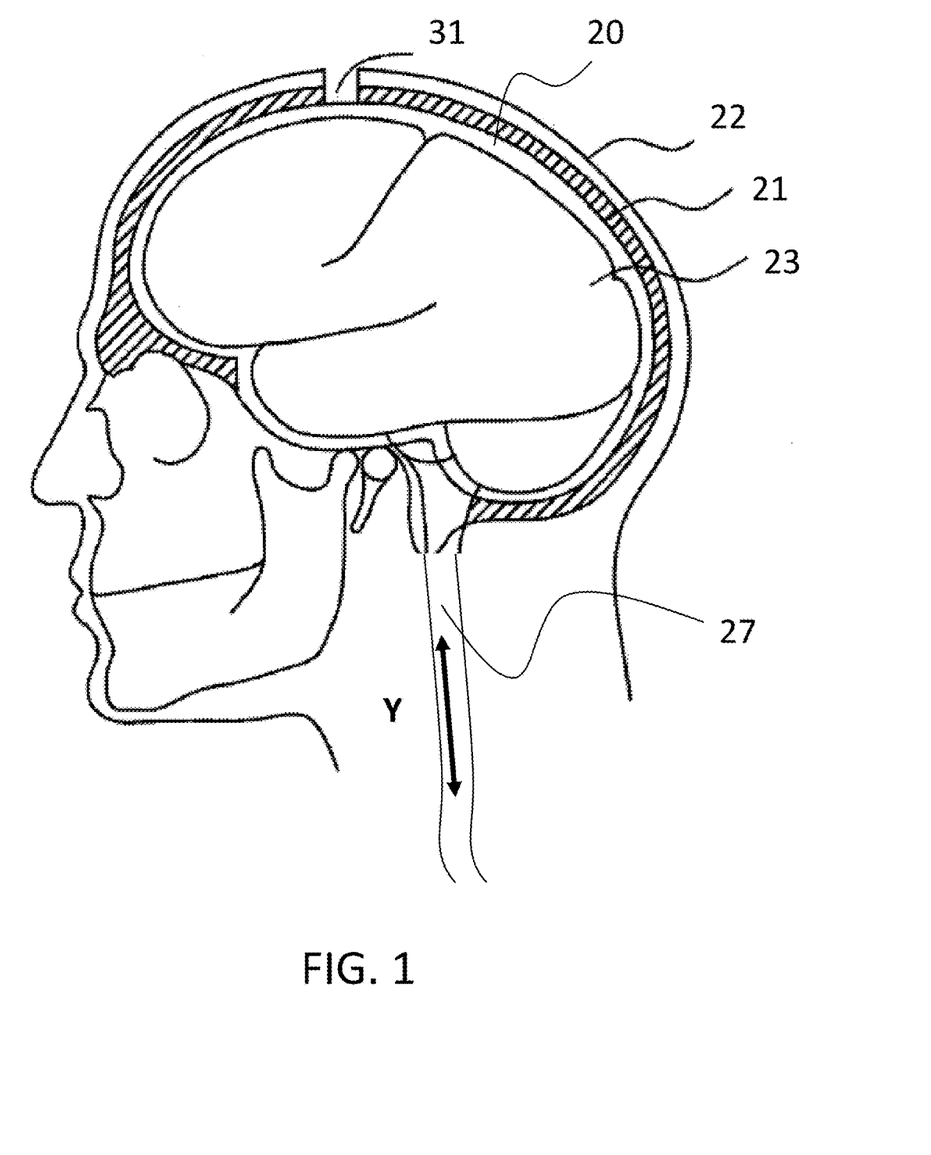
FIG. 1 is a side cross section (longitudinal or sagittal section) of a patient depicting an exemplary embodiment of a method in accordance with the disclosed subject matter.
Figure 2A:
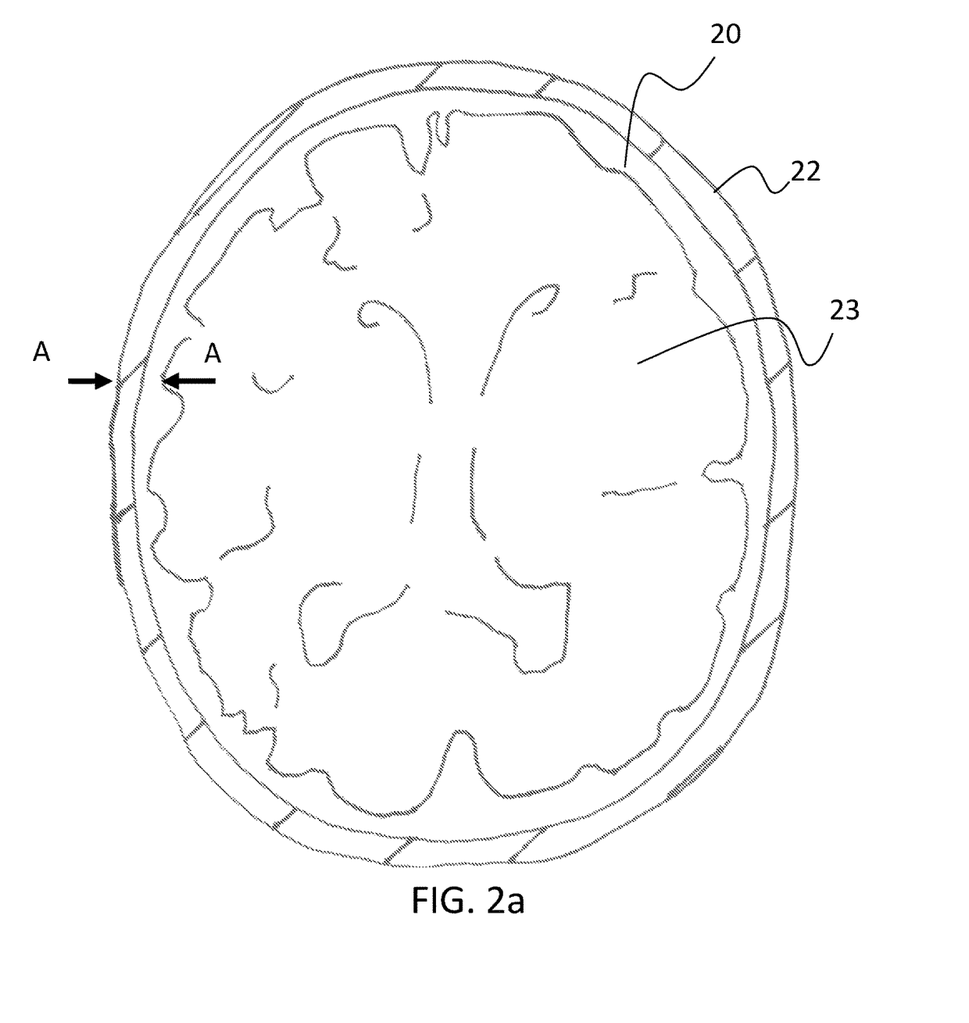
FIG. 2a is a top (horizontal) cross sectional view of a healthy human brain located within the cranium.
Figure 2B:
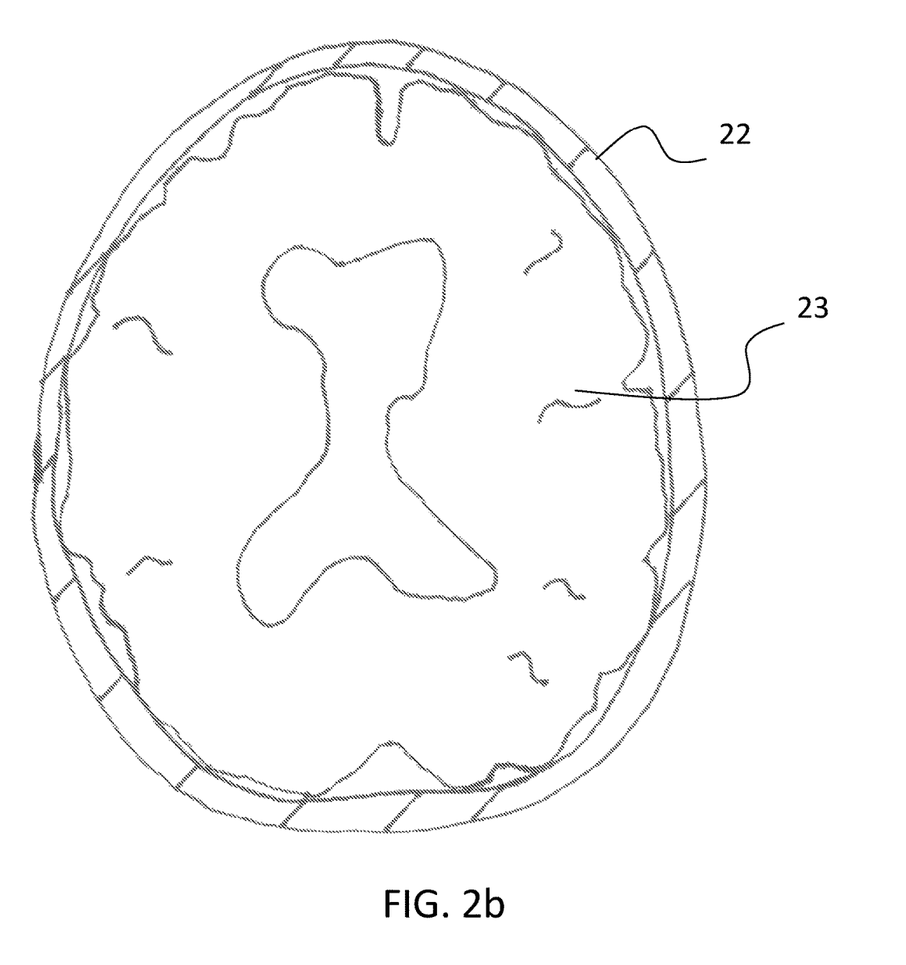
FIG. 2b is a top cross sectional view of a human brain experiencing initial expansion of the ventricles as in hydrocephalus and located within the cranium.
Figure 2C:
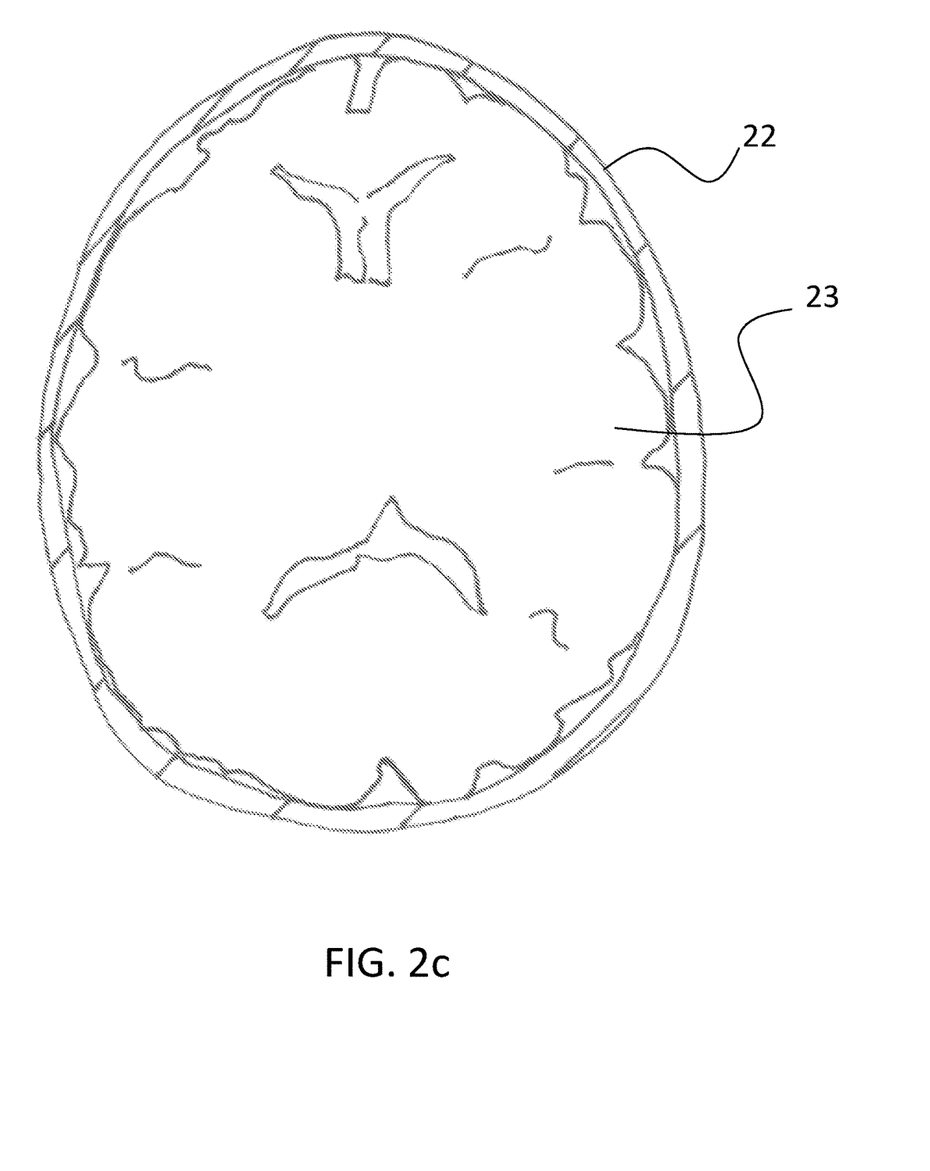
FIG. 2c is a top cross sectional view of a human brain experiencing advanced swelling resulting in ventricular collapse and located within the cranium.

Expansion of the ventricles of the brain with CSF or of solid tissue in the cranium in theory cause a sequential series of increases in ICP. FIG. 2a shows a superior transverse cross-section of a brain 23 located within CSF 21, both of which are encapsulated by the skull 22. In this drawing, arrows A-A denotes the cushion of CSF which decreases as the brain swelling begins. This condition is referred to as a green status. FIG. 2b shows the point at which the brain has swollen to the extent at which a portion of the brain 23 contacts the skull 22 and the layer of CSF 21 surrounding the brain is non-existent (at least at certain points). This condition is referred to as orange status. FIG. 2c shows the collapse of the fluid filled ventricles located within the brain after the brain has swollen and substantially filled the calvarium. This condition is referred to as blue status. The final condition, red status, is schematically represented in FIG. 1 in that the arrow Y shows that the brain stem 27 will begin traversing out of its normal position. In this case, ICP measured for example by a manometer at opening 31 in the skull will be seen to significantly increase.

The arrow Y shown in FIG. 1 depicts the downward displacement of the brain stem 27 through the foramen magnum once the brain has swollen to a volume that can no longer be contained within the calvarium of the skull 22. Because of the differing mechanical properties of these 3 volume accommodations shown in FIGS. 2a-2c, the pressure/volume relationship for each is expected to be different resulting in a relationship of increasing slope, as shown in FIG. 3.

Figure 3:
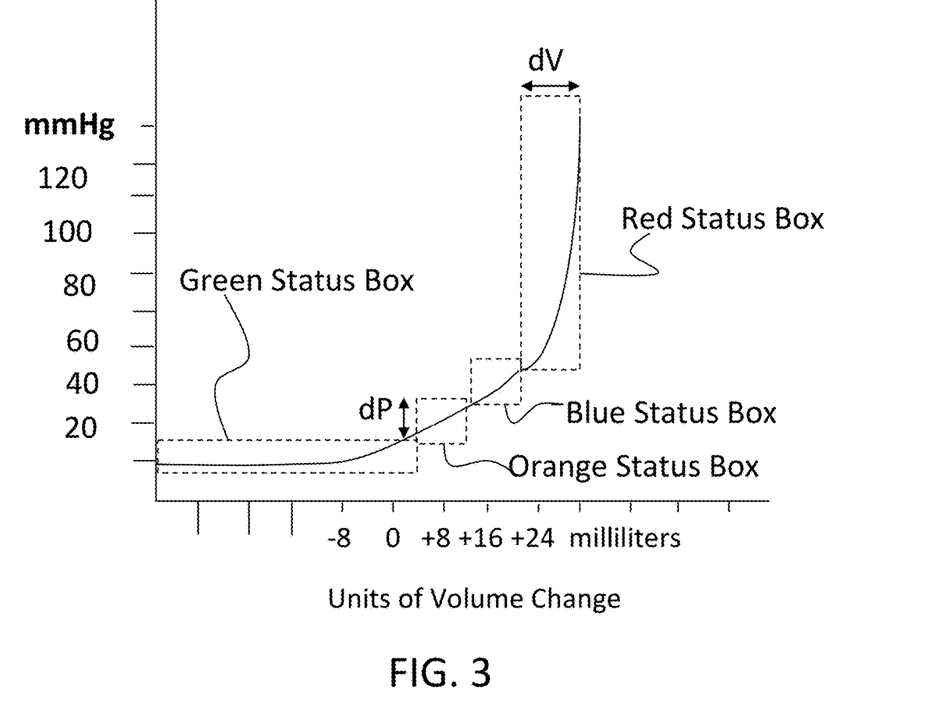
FIG. 3 is a graphical representation of the relationship between expansion of the tissues and/or fluids within the calvarium (on the horizontal axis) and the increase in intracranial pressure (shown on the vertical axis in mmHg).

In FIG. 3, as the solid materials in the calvarium increase in volume (swelling caused by brain edema, expanding tumor, or expanding hematoma, for example) and as contained volumes expand (CSF outflow obstruction expanding ventricles (hydrocephalus), the marginal fluid, the endocranial CSF thins (low elastance dP/dV), as shown in the green status box. In the absence of endocranial CSF (orange status box), the ventricles deflate through their normal drainage path via the fourth ventricle (moderate elastance dP/dV) until complete collapse of the superior ventricles (blue status box). Finally, after the superior ventricles have collapsed, subsequent changes in volume are accommodated by axial motion of the brain stem (high elastance dP/dV) out of the calvarium (red status box), and as depicted by path Y shown in FIG. 1.

Figure 4:
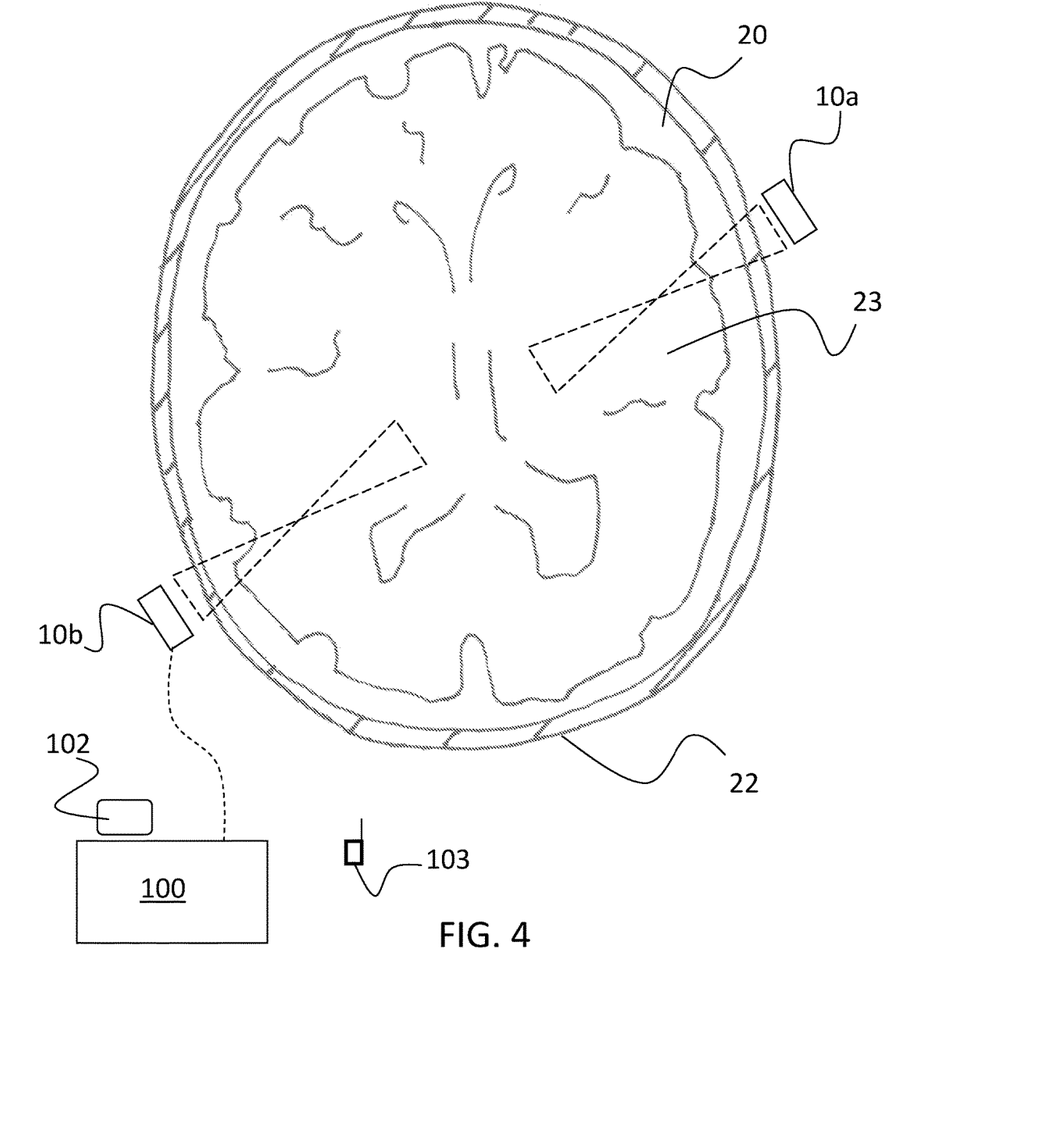
FIG. 4 is a top cross-sectional view of a human brain and exemplary embodiment of an apparatus made in accordance with principles of the disclosed subject matter.

These sequential steps can be identified using TransCranial Brain Tissue Doppler (TCBTD) by the characteristic lateral pulsatile motions of the brain at a series of depths and the motion of the brain stem (FIG. 4).

One advantage of TransCranial Brain Tissue Doppler over conventional TransCranial Blood Tissue Doppler is that the echogenicity of solid brain tissue is 30 dB (1000 times) greater than the echogenicity of blood so that the ultrasound transducer can transmit pulses and receive echoes through thick regions of the skull rather than only through the thin temporal window of the skull just above and anterior to the ear as is required for conventional TransCranial Blood Doppler.

As solid brain tissue swells due to edema, hematoma or tumor, natural brain motions change. Initially, in the normal brain, the two cerebral hemispheres move laterally about 30 microns (GREEN STATUS BOX, FIG. 2a) displacing the endocranial marginal CSF layer as the arterioles and arteries fill in systole; the hemispheres return centrally during diastole.

With mild swelling, the marginal CSF layer is displaced into the spinal cord, fixing the brain surface against the cranium preventing lateral motion (ORANGE STATUS BOX, FIG. 2b). The pulsating arterioles and arteries in the brain compress the central brain ventricles with a pulsatile waveform.

With moderate brain swelling, the brain ventricles are compressed, displacing the contained CSF into the spinal cord and the venous blood into the sub-cranial circulation, preventing the pulsatile compression of the brain ventricles (BLUE STATUS BOX, FIG. 2c). This is the beginning of elevated ICP.

Because fluid motion into and out of the brain ventricles is restricted compared to the marginal CSF, the "brain compliance" (compliance=dV/dP) appears to be lower.

If the expansion continues, then the brain arteriolar pulsations are accommodated only by motions of the brain stem, which is constrained by tethers and by the outlet dimensions resulting in a high "brain compliance." This is severe ICP.

Figure 8A:
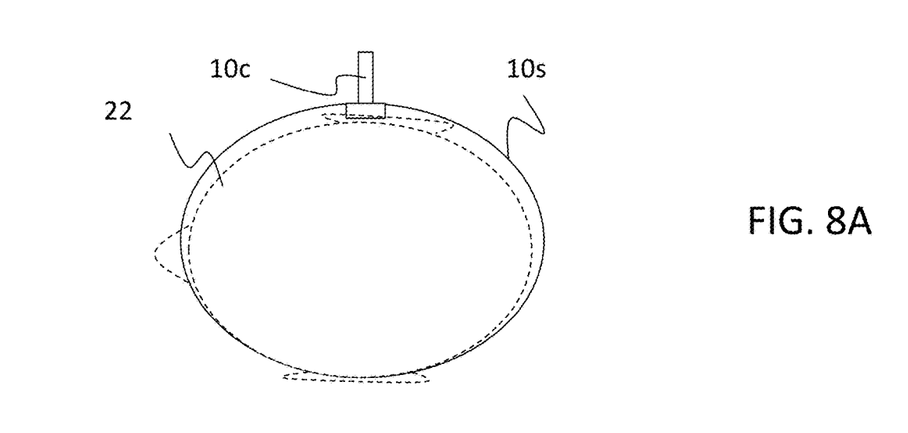
FIGS. 8A and 8B are top schematic views show a transducer and attachment structure for attachment long term attachment to a human skull.
Figure 8B:
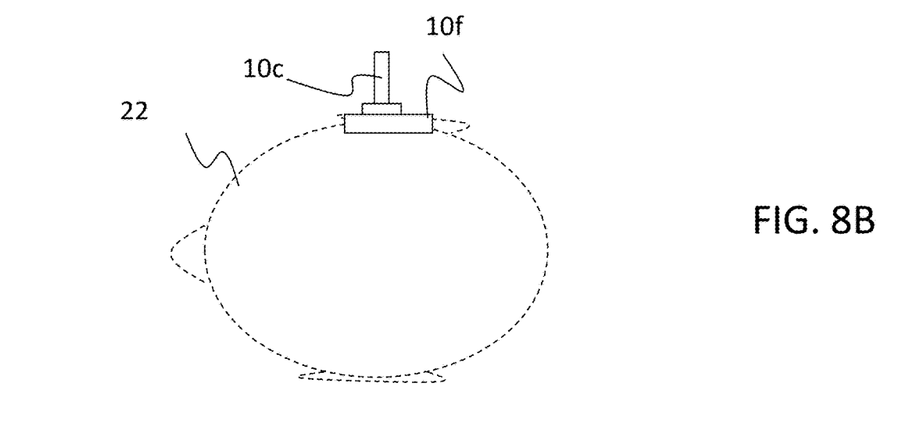

FIG. 4 shows an exemplary apparatus for use in monitoring and determining brain swelling in accordance with the disclosed subject matter. In this embodiment, a controller 100 is connected to at least one transducer (for example, two ultrasound transducers 10a and 10b). The ultrasound transducers 10a and 10b can be mountable or positionable adjacent either side of a patient's skull for directing and receiving ultrasound transmissions and reflections at various angles and at various depths into the skull. Alternatively, one or more ultrasound transducer(s) 10a, 10b can be placed on the forehead, where the attachment and transmission is not impeded by hair. An adhesive transducer can be used for attachment to the forehead. The forehead mount using adhesive can help remove user inputs/variables. In particular, the transducer(s) 10a, 10b can be configured to view the optimum areas of intracranial tissue when adhered directly to a user's forehead. As shown in FIG. 8A, the attachment structure can be configured as a separate strap 10s that can be configured as an elastic band or similar mechanical mounting device that is configured to keep the transducer 10c located, positioned and targeted for a relatively long time period, and on the order of multiple days if necessary. As shown in FIG. 8B, the attachment structure can be configured as an adhesive 10f that can be configured as an adhesive chemical/material that is coated on a mounting surface of the transducer 10c and can thus be adhered to a patient's skull, and for example, to a shaved portion of a patient's head. The adhesive 10f can also take the form of a bandage made from fabric, plastic, metal, or the like that extends from the transducer 10c and is configured to keep the transducer 10c located, positioned and targeted for a relatively long time period relative to the patient's head.

The ultrasound transducers 10a and 10b can be "communicatively connected" to the controller 100 by a hard wire connection (such as metal wire, fiber optics, or other hard connection) or by a wireless connection (such as wi-fi, bluetooth technologies, and other radio-frequency connections or other wireless communication protocols). In operation, the controller 100 can be integrated into or separate from a typical ultrasound device, and includes software and or hardware configured to obtain, determine and/or monitor the location of a first brain tissue portion relative to a second brain tissue portion. The software and/or hardware can be configured such that positional information of a first target tissue is obtained and then compared to positional information related to a second target tissue. If the information indicates an expected pulsation over time with the cardiac cycle, then the controller 100 will determine that the brain is free to expand normally. If the information indicates a periodic expansion with respiration, then the controller 100 will determine that the venous pressure in brain exceeds the intracranial pressure, which is normal in a supine patient. If the information indicates a change of position over time in concert with an accelerometer monitoring skull position and/or orientation, then the controller 100 will determine that the brain is folating normally in the CSF. If the information indicates a progressive change over time, then the controller 100 will determine that the brain is swelling. If the information indicates either a decrease in change over time, or indicated no relative movement after a period of movement, then the controller 100 will determine that the brain is swelling and that ICP will increase in the near future. Upon the controller 100 determining that ICP will increase, information can be provided to a practitioner via a monitor 102 or via a remote alarm device 103 such that the practitioner will be informed that ICP will likely increase in the patient. The monitor device 102 can be built into or attached to the controller 100 either via a wired or wireless connection. Similarly, the alarm device 103 can be attached to the controller 100 either via a wired or wireless connection. Alternatively, the alarm device 103 can be a cell phone or other type of remote communication device. The controller 100 can also be configured to provide information to a server that then manages the information and communicates to various recipients (such as alarm device 103 in the form of a cellular phone, tablet, computer, etc.). Various applications can also be developed to best manage and deliver the information to specific remote devices.

It should be noted that radio frequency phase demodulation can be used in the disclosed subject matter to obtain the desired resolution from the ultrasound (or other) transducer 10c. For example, resolution can be such that 1/10 micron displacements can be measured within the brain tissue.

The controller 100 can also be connected to other sensors to provide for more accurate determination of positional relationships of brain tissue relative to itself (i.e., to determine the amount of change in position of a first target brain tissue relative to a second target brain tissue to determine swelling, etc.). For example, an accelerometer 107 can be provided and attached to a patient's head and/or chest (over the sternum) to monitor position and movement of these two areas of the body such that the movement can be used to better calculate the positional relationship between the two target brain tissues or the elevation between a target brain tissue and the right atrium of the heart which is used as a pressure reference. More specifically, the accelerometers 107 placed on the skull and sternum can be used to determine a relative elevational difference between the right atrium and the body part being measured, e.g., skull/brain. In addition, a respiratory and/or a pulmonary sensor can be attached to the controller 100 such that respiratory and/or a pulmonary function information can be used to better calculate the positional relationship between the two target brain tissues, and to better the existence of swelling. In one example, the respiratory and/or a pulmonary sensor can be combined with either the accelerometer 107 or the ECG sensor(s) 105s. Recently, microcircuit patches have become available that attach to a user's head like a small bandage and wirelessly transmits acceleration data for real-time monitoring of head acceleration, especially during sporting activities. It is contemplated that the accelerometer 107 can be configured in a similar manner to include such a microcircuit. In addition, because swelling of the brain tissue is relatively small, and because there is a great deal of variability between anatomical geometry in patients, it may be helpful to use base line data to ensure greater accuracy of swelling and positional measurement and calculation. For example, base line data including skull and brain location data is sometimes collected for athletes. This type of base line information could then be utilized by the system/apparatus 1 of the disclosed subject matter to increase accuracy during use on a particular patient in which base line information is available.

Figure 5:
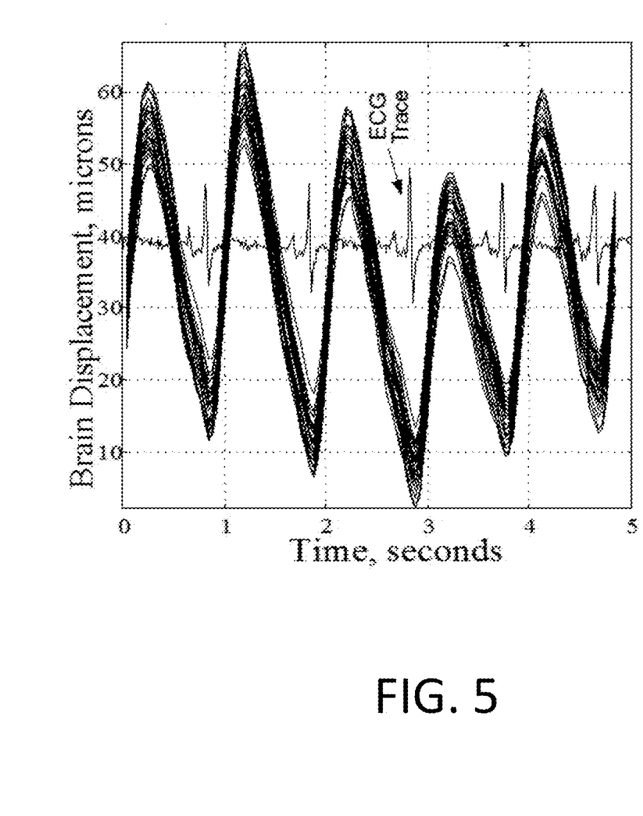
FIG. 5 is a graph showing intracranial tissue displacement in microns vs. time of a patient superimposed over the ECG of the patient.

FIG. 5 is a graph showing intracranial tissue displacement of a patient in microns vs. time superimposed over an electrocardiograph (ECG) trace of the patient. In this graph, the patient's head is motionless and accelerometers 107 record movement of the head to determine that no skull motion occurs during this period. An ultrasound transducer is placed adjacent the temporal area of the skull and records motion and location of tissue located within the skull over time. The graph shows motion of tissue within the skull over time as indicated by the dark generally sinusoidal wave form. An ECG of the patient is simultaneously taken while the ultrasound results are graphed, and is superimposed on top of the ultrasound plot. The resulting graph shows a unique relationship between a patient's cardiac function and motion of intracranial tissue, and demonstrates the natural pulsatile motion of brain (and other intracranial tissue). By understanding the relationship of cardiac function relative to tissue motion, one can then correct for the motion that is solely due to cardiac functions to enable a more precise calculation or determination of motion (or location) of intracranial tissue due to the type of tissue swelling that is predictive of increases in ICP.

Figure 6A:
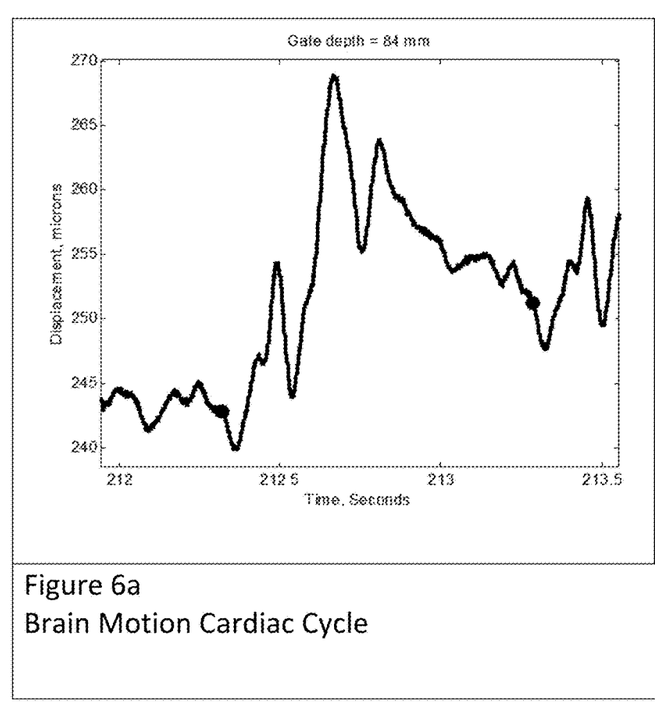
FIGS. 6a and 6b are graphs plotting displacement of tissue in microns vs. time in order to show: Brain Motion Cardiac Cycle; and Respiratory Cycle, respectively, with Black Spots depicting ECG-QRS for timing.
Figure 6B:
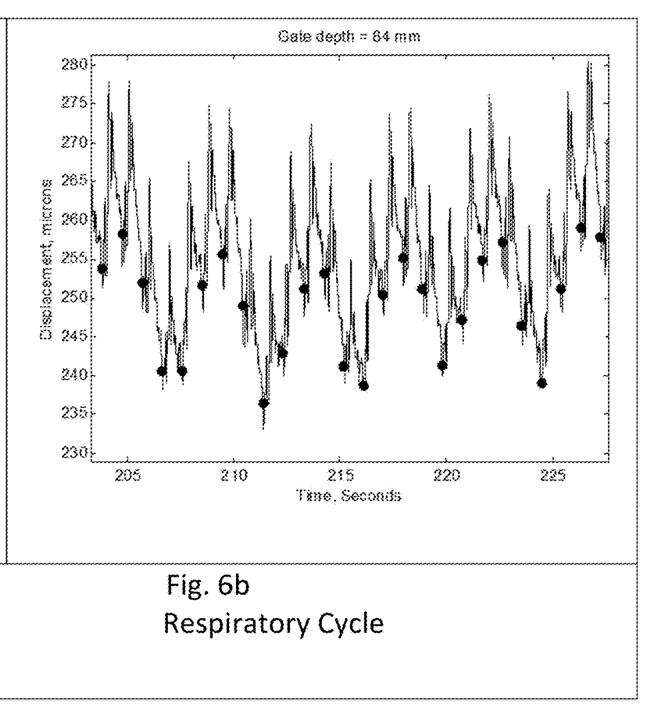

FIGS. 6a and 6b are graphs plotting displacement of tissue in microns vs. time in order to show Brain Motion Cardiac Cycle (FIG. 6a) and Respiratory Cycle (FIG. 6b). The Black Spots in FIGS. 6a and 6b depict ECG-QRS for timing. By understanding the relationship of both cardiac and respiratory functions relative to tissue motion, one can then correct for each of these types of motions when trying to calculate or determine motion (or location) of intracranial tissue due to the type of tissue swelling that is predictive of increases in ICP. These motions can also be used to infer the relationship between venous/venular pressure and ICP and between systolic and diastolic arterial blood pressure (DBP, SBP) and ICP. For instance, if the ICP is elevated to a level between SBP and DBP, both the displacement pulsations and the differential displacement (strain) pulsations will be greater than when the ICP is below the DBP because the arteries and arterioles will collapse in diastole. If ICP exceeds SBP, then pulsations would cease.

Intracranial tissue, including brain tissue, exhibits natural pulsatile motions. In an upright normal person, the cardiac motion is about 20 micrometers superimposed on the respiratory motion of about 20 micrometers. The motion includes the dicrotic wave commonly found in any plethysmographic method. The presence of the dicrotic wave indicates relative vasoconstriction, and loss of this wave indicates relative vasodilation. The respiratory motion in an upright person is likely due to changes in cardiac output with respiration as the central venous pressure is less than the elevation of the head over the heart. If the person is supine, then an additional respiratory component may be present, with a different phase than the cardiac output component. The motion is bilateral, and thus the ventricles expand.

As shown in FIGS. 6a and 6b, the brain (and other intracranial tissue) expands and contracts over both the cardiac and respiratory cycles. However, brain volume is constrained by the skull (and other tether points, as described above). Expansion or swelling of the brain or other intracranial tissue compresses the ventricles in the brain. Each cardiac cycle causes the brain to move medially, posteriorly, and caudally. These motions are the basis of the monitoring system proposed for determining intracranial tissue swelling, which is the cause of increased intracranial pressure in most cases.

Figure 7:
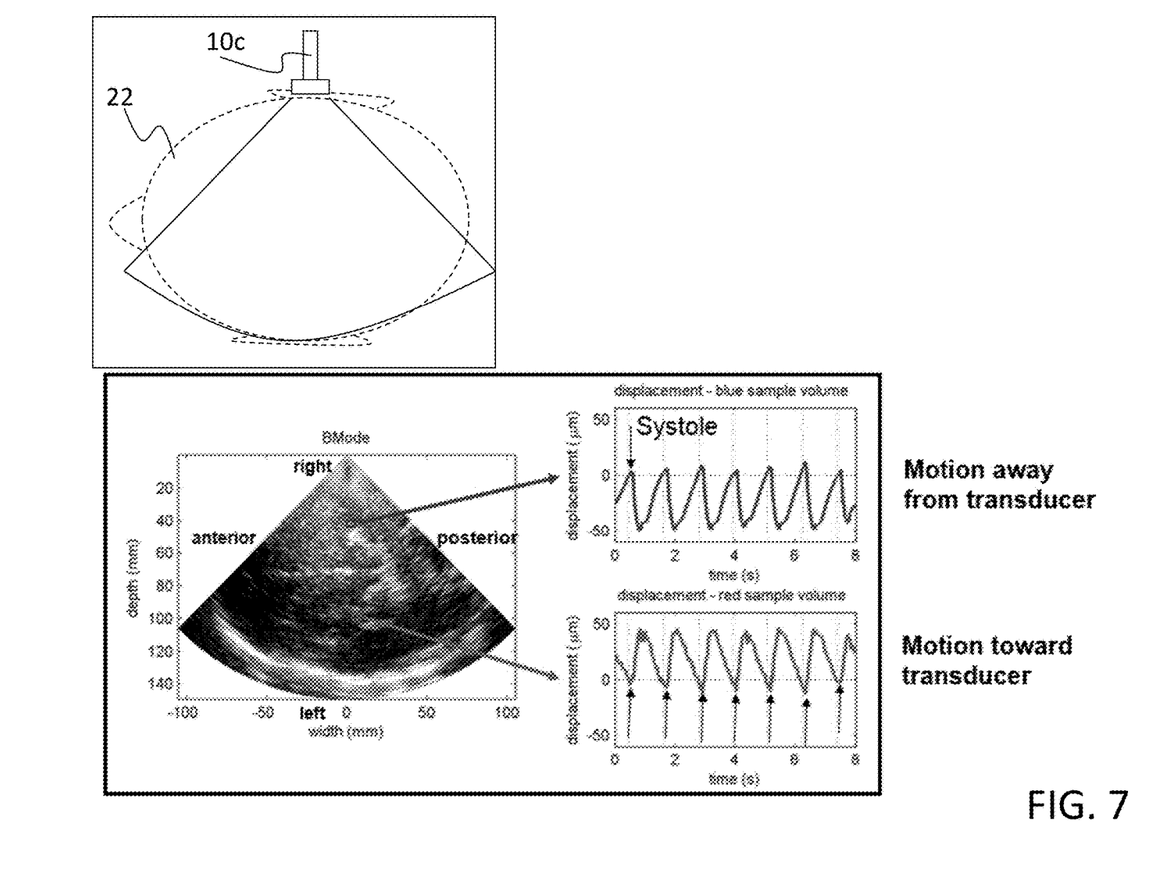
FIG. 7 is a schematic showing a cross-section of a 2-dimensional ultrasound scanhead directed through a human skull along with two graphs showing bilateral cerebral expansion away from the transducer (upper graph) and toward the transducer (lower graph).

FIG. 7 is a schematic showing a cross-section of an ultrasound transducer or scanhead penetrating through a human skull 22 along with two graphs showing bilateral cerebral expansion away from the transducer 10c (upper graph) and toward the transducer 10c (lower graph). As can be seen from these graphs, the pulsatile nature of the movement of various tissue within the skull is pulsatile in nature, and predictable, when a patient's cardiac and respiratory functions are monitored. In this image, the reflective falx cerebri can be seen as a horizontal bright line midway between the blue and red voxel boxes. It should be understood that a single beam transducer can be a single element sending out a single beam, as in most of this work; a scanhead transducer is able to direct a series of beams along different paths to gather data from a 2 dimensional plane (or volume) to form a 2-D image. In the case in which a scanhead is used, an array of sequential ultrasound beam patterns will be displayed radiating from the scanhead 10*c*.

Figure 9:
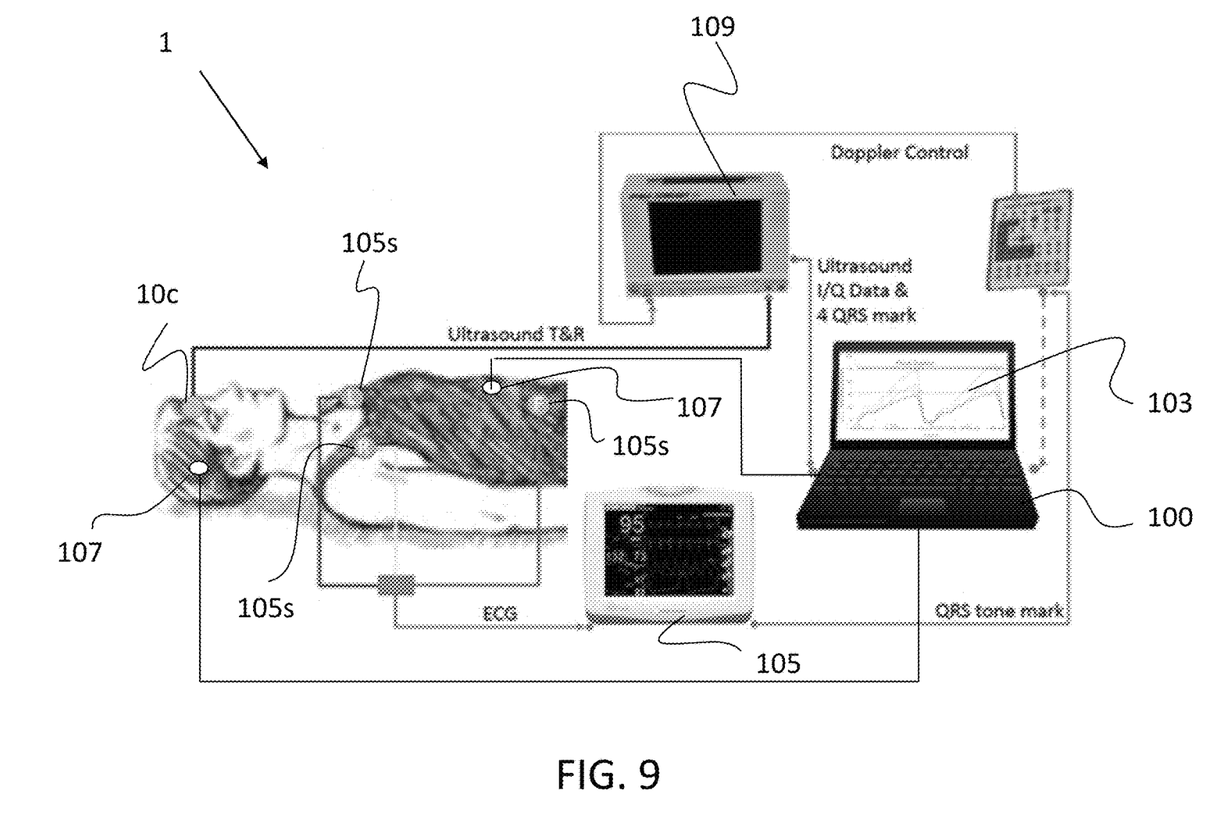
FIG. 9 is a schematic view of a system for detecting intracranial pressure according to an embodiment of the disclosed subject matter.

FIG. 9 is a schematic view of a system/apparatus 1 for detecting intracranial pressure according to an embodiment of the disclosed subject matter. The system/apparatus 1 can include a transducer 10*c* such as a scanhead, or other ultrasound, optical or impedance transducer device that is either electrically or wirelessly connected in communication with controller 100. An ultrasound or other imaging device 109 can also be connected in a similar manner to controller 100, and can be configured to take information from the one or more sensors 10*c* and manipulate/calculate that information and transmit that information to the controller 100. The system/apparatus 1 can also include a series of accelerometers 107 positioned, for example, at the skull and at the sternum of the patient and in communication with the controller 100 to relay information to the controller 100 related to position, movement and orientation of the patient. An ECG device 105 can also be connected either by wire or wirelessly to controller 100, and can include a plurality of sensors 105*s* as is known in the ECG device art for obtaining and transmitting information related to the patient's cardiac function, including cardiac cycle information. An alarm device 103 can be in the form of a monitor screen for the controller 100, but can also be a separate device that the user can carry or place at a location as desired. The actual alarm can be in the form of information directed to the monitor, but can also be other visible, audible or other sensory alarm mechanisms that inform the user of the status of the patient, for example, provide information to the user alerting the user when intracranial pressure is likely to increase in a patient.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. An apparatus for predicting intracranial pressure increase in a patient, comprising:
    a transducer configured for attachment to the patient's head;
    at least one of a monitor and an alarm device; and
    a controller communicatively connected to both the transducer and the at least one of the monitor and the alarm device, the controller configured to receive information from the transducer related to at least one of a location and a motion of a first tissue portion relative to at least one of a location and a motion of a second tissue portion,
    the controller further configured to predict an increase in the volume of an intracranial structure of the patient or intracranial pressure of the patient based on information that motion of the first tissue portion relative to the second tissue portion at a first time occurs at a first value that correlates to expansion of brain tissue, and at a second time occurs at a second value less than the first value that correlates to a decrease in motion of the brain tissue caused by the brain tissue contacting an intracranial structure, and the controller configured to output a signal to the at least one of the monitor and the alarm device if the controller predicts the increase in the volume of an intracranial structure or intracranial pressure.

2. The method of claim 1, wherein the transducer is an ultrasound transducer.

3. The apparatus of claim 1, further comprising:
    at least one accelerometer communicatively connected to the controller, the at least one accelerometer configured for attachment to at least one of the chest and the head of the patient.

4. The apparatus of claim 3, wherein the controller is configured to receive information from the at least one accelerometer and to use the information to determine whether motion of the first tissue portion is due to brain swelling or due to movement of at least one of the chest and head of the patient.

5. The apparatus of claim 1, further comprising:
    a respiratory sensor communicatively connected to the controller and configured to determine a respiratory function of the patient.

6. The apparatus of claim 1, further comprising:
    a cardiac sensor communicatively connected to the controller and configured to determine a cardiac function of the patient.

7. The apparatus of claim 1, further comprising:
    a respiratory sensor communicatively connected to the controller and configured to obtain respiratory information related to a respiratory function of the patient; and
    a cardiac sensor communicatively connected to the controller and configured to obtain cardiac information related to a cardiac function of the patient, wherein
    the controller is configured to use the respiratory information and the cardiac information to calculate at least one of location and motion of the first tissue portion.

8. The apparatus of claim 1, wherein the first tissue portion is a first brain tissue portion, and the second tissue portion is a second brain tissue portion different from the first brain tissue portion.

* * * * *